United States Patent [19]
Goodale et al.

[11] Patent Number: 5,605,666
[45] Date of Patent: *Feb. 25, 1997

[54] CAPILLARY RETAINING SYSTEM

[75] Inventors: David L. Goodale; Duane G. Barber, both of Yorba Linda; Richard C. Meyer, Lahabra, all of Calif.

[73] Assignee: Beckman Instruments, Inc., Fullerton, Calif.

[*] Notice: The term of this patent shall not extend beyond the expiration date of Pat. No. 5,417,925.

[21] Appl. No.: 410,036

[22] Filed: Mar. 23, 1995

Related U.S. Application Data

[63] Continuation-in-part of Ser. No. 71,832, Jun. 3, 1993, Pat. No. 5,417,925, which is a continuation of Ser. No. 48,709, Apr. 16, 1993, abandoned.

[51] Int. Cl.$^6$ ........................................... B01L 11/00
[52] U.S. Cl. ........................... 422/103; 422/100; 422/104; 204/452; 204/453; 204/603
[58] Field of Search ................... 422/82.05, 99, 422/100, 103, 104; 436/164, 165, 180; 204/180.1, 183.3, 299 R, 452, 453, 603; 96/106

[56] References Cited

U.S. PATENT DOCUMENTS

| | | | |
|---|---|---|---|
| 3,779,083 | 12/1973 | Ayres et al. | 422/100 X |
| 3,867,271 | 2/1975 | Hoefer | 204/456 |
| 4,048,049 | 9/1977 | Hoefer | 204/606 |
| 4,375,401 | 3/1983 | Catsimpoolas | 204/607 |
| 4,788,150 | 11/1988 | Nelson et al. | 436/45 |
| 5,019,236 | 5/1991 | Young | 204/601 |
| 5,045,172 | 9/1991 | Guzman | 204/452 |
| 5,110,431 | 5/1992 | Moring | 204/451 |
| 5,126,023 | 6/1992 | Huang et al. | 204/453 |
| 5,173,163 | 12/1992 | Tehrani | 204/452 |
| 5,198,091 | 3/1993 | Burolla et al. | 204/601 |
| 5,202,010 | 4/1993 | Guzman | 204/601 |
| 5,207,886 | 5/1993 | Lauer et al. | 204/604 |
| 5,227,138 | 7/1993 | Boyd et al. | 422/99 X |
| 5,302,272 | 4/1994 | Klein | 204/603 |
| 5,312,535 | 5/1994 | Waska et al. | 204/603 |
| 5,356,525 | 10/1994 | Goodale et al. | 204/602 |
| 5,413,686 | 5/1995 | Klein et al. | 204/603 |
| 5,417,925 | 5/1995 | Goodale et al. | 422/103 |

FOREIGN PATENT DOCUMENTS

| | | |
|---|---|---|
| 0339779 | 3/1989 | European Pat. Off. . |
| 0443320 | 1/1991 | European Pat. Off. . |
| 3939858 | 6/1990 | Germany . |
| 4230354 | 3/1993 | Germany . |
| 8904966 | 6/1989 | WIPO . |

*Primary Examiner*—Jill Warden
*Assistant Examiner*—Maureen M. Wallenhorst
*Attorney, Agent, or Firm*—William H. May; Gary T. Hampson; Sheldon & Mak

[57] ABSTRACT

A capillary and capillary retaining system including a capillary assembly having first and second end holders. The first and second end holders are adapted to be received by first and second retainers. The first end holder may include protruding portions and the first end retainer includes clips or clamps to engage the protruding portions. The second end holder may include opposite recesses and the second retainer is adapted to receive optical cables that are received within the recesses to retain the second end holder. The second retainer can further include a lever on the retainer body to pry the second holder out of the second retainer. Locks or clips retained by the second end retainer cooperate with grooves in the optical cables to retain the optical cables.

53 Claims, 10 Drawing Sheets

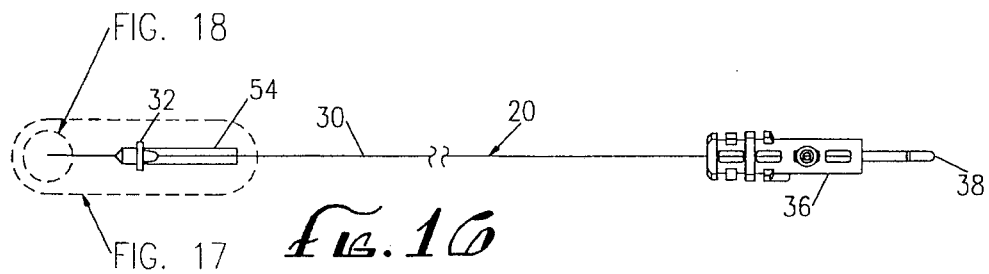
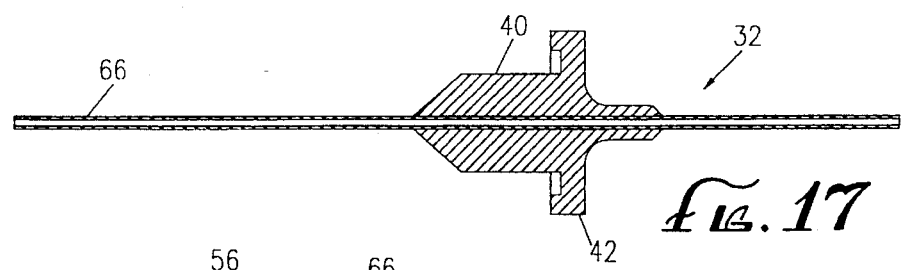
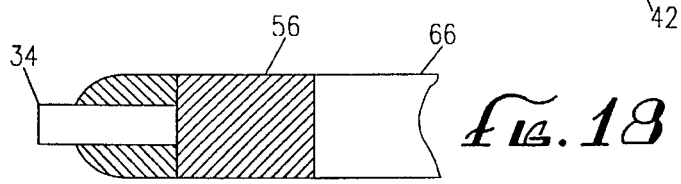
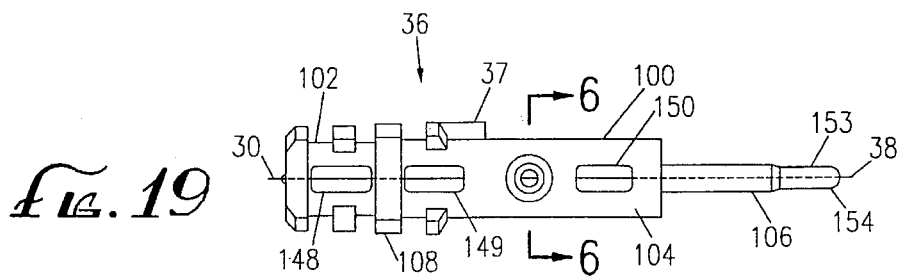
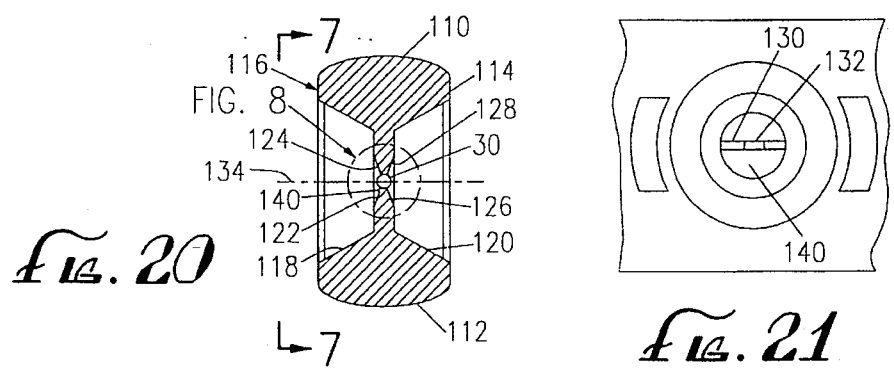

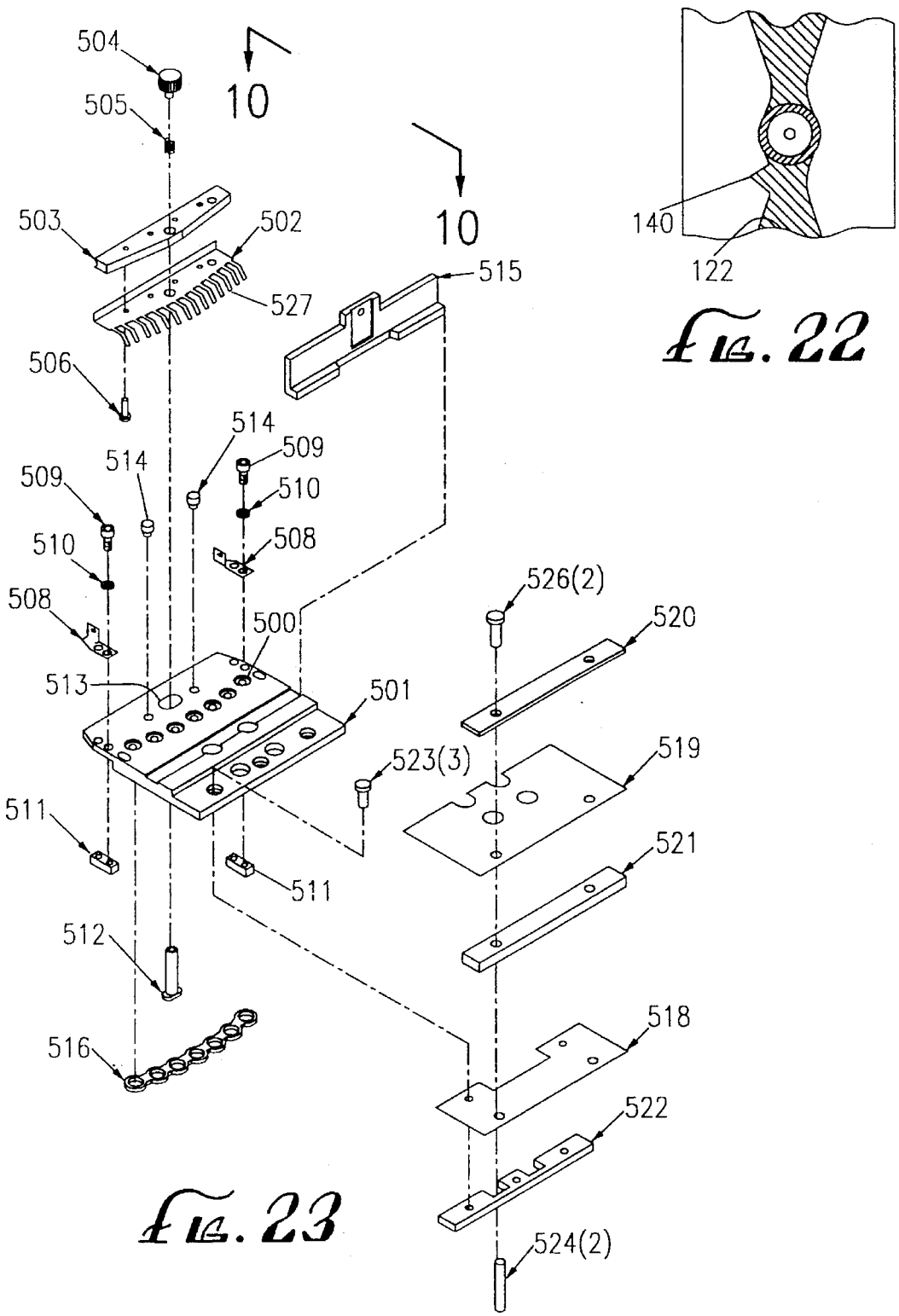

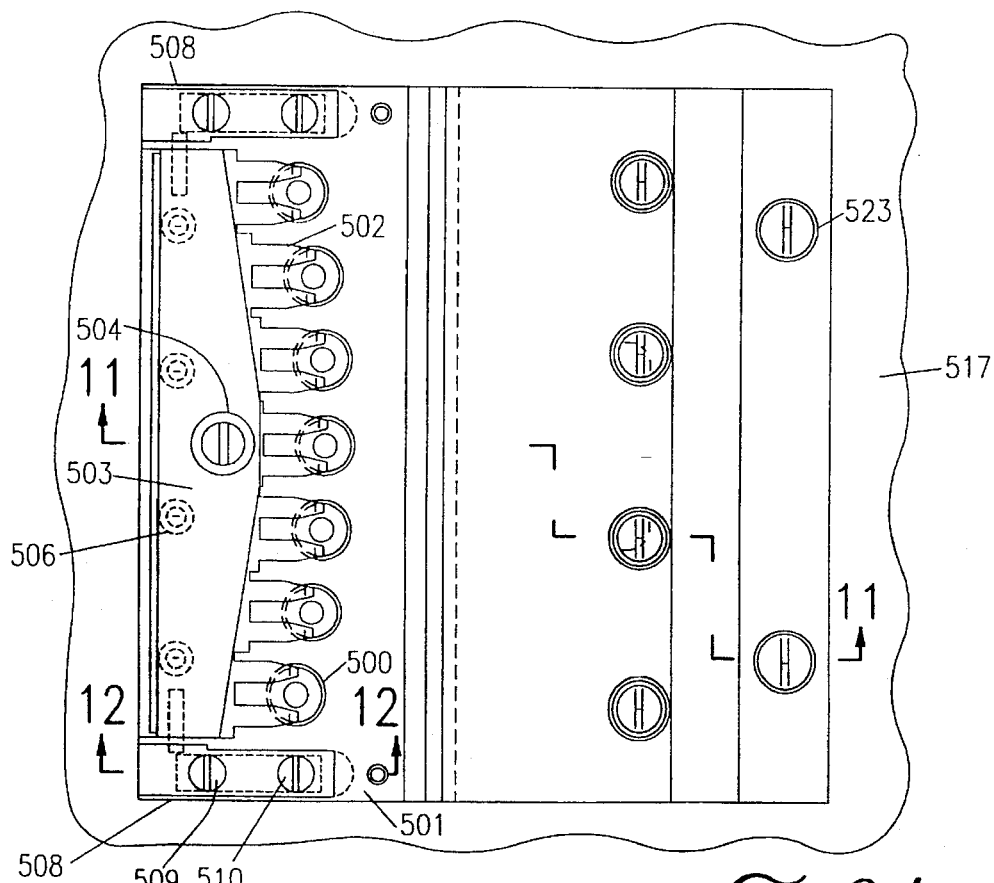
fig. 24
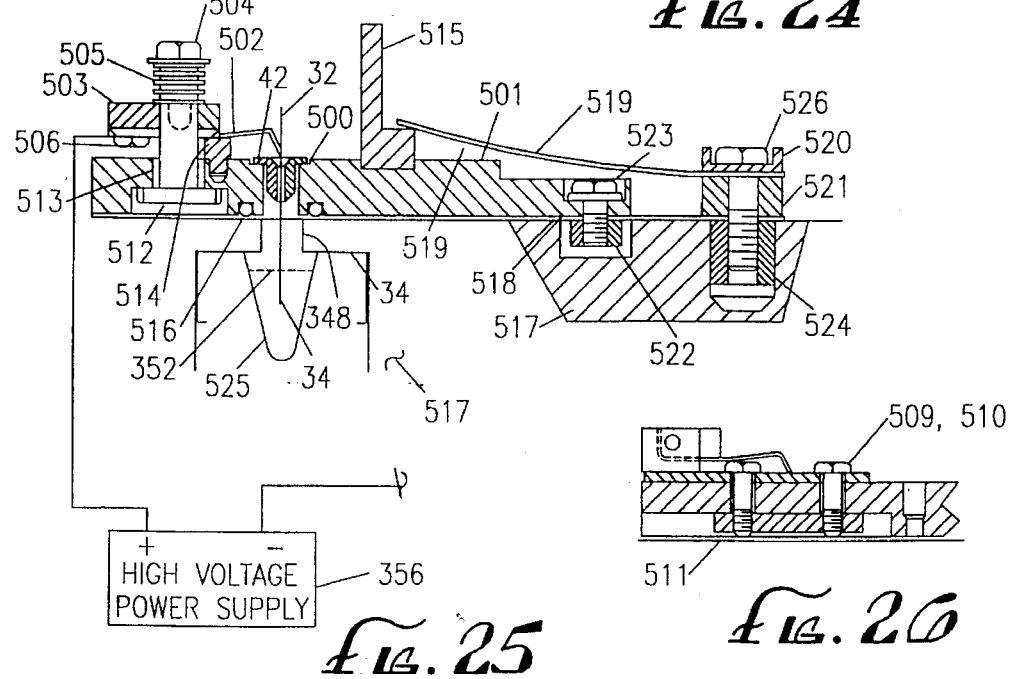
fig. 25
fig. 26

CAPILLARY RETAINING SYSTEM

This application is a continuation-in-part of U.S. patent application Ser. No. 08/071,832 filed Jun. 3, 1993, now U.S. Pat. No. 5,417,925, issued May 23, 1995, which is a continuation of U.S. application Ser. No. 08/048,709, filed Apr. 16, 1993 now abandoned.

The present application is related to the following applications that are commonly assigned and filed concurrently herewith, and which are incorporated herein by reference:

U.S. patent application Ser. No. 08/072,202 filed Jun. 3, 1993, now U.S. Pat. No. 5,356,525, issued Oct. 18, 1994 entitled "Sample Handling System", filed in the names of David L. Goodale and Steven D. Mack, which is a continuation of U.S. patent application Ser. No. 08/048,708, filed Apr. 16, 1993, and now abandoned.

U.S. patent application Ser. No. 08/071,831, filed Jun. 3, 1993, now abandoned entitled "Sample Segment", filed in the names of Ronald C. Glenday, David L. Goodale and Steven D. Mack, which is a continuation of U.S. patent application Ser. No. 08/048,716, filed Apr. 16, 1993, now abandoned.

FIELD

The present application is related to the field of capillary electrophoresis.

BACKGROUND

The value of capillary electrophoresis as a separation and analytical technique has been recognized for some time. In capillary electrophoresis, a small tube or capillary is filled with an electrically conductive fluid, or buffer. A small quantity of a sample to be analyzed is introduced into one end of the capillary bore, the ends of the capillary are placed into separate reservoirs of buffer, and a direct current high voltage is applied to the ends of the capillary by means of electrodes positioned in the buffer reservoirs, causing a small current to flow through the capillary.

With the correct polarity applied across the capillary, the sample begins to migrate toward the other end of the capillary. As this migration occurs, different molecules in the sample travel at different rates, causing the sample to become separated into bands of these different molecules. These bands or groups of different molecules are detected near the other end of the capillary by, for example, passing a perpendicular light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

Capillary electrophoresis analyzers typically use a single capillary to perform an analysis. For example, European Patent Application number 89302489.3, publication number 0,339,779 A2, corresponding to U.S. patent application Ser. No. 07/188,773, filed Apr. 29, 1988 (Burolla) now abandoned, describes an automated capillary electrophoresis apparatus using a single capillary, as does U.S. Pat. No. 5,045,172 to Guzman. To increase throughput, however, a plurality of capillaries may be utilized in parallel, thus performing a corresponding plurality of capillary electrophoresis analyze simultaneously. An analysis employing parallel capillaries is disclosed, for example, in U.S. patent application Ser. No. 07/916,308 filed Jul. 17, 1992 issued as U.S. Pat. No. 5,413,686 on May 9, 1995, and entitled "Multi-Channel Capillary Electrophoresis Systems."

In such an analyzer, there is a need for easy replacement of the capillaries. Such replacement should be possible without the use of special tools. Further, the capillaries should occupy a relatively small volume within such an analyzer, and thus the capillaries should be as closely spaced as possible while retaining each capillary in a fashion that allows replacement by hand. Due to the closely spaced nature of such capillaries, there is also a need for capillaries that can be easily replaced in such a confined space with relatively little manipulation, which is particularly important given the extremely small diameter of such capillaries.

Thus, there is a need for capillaries and a capillary retaining system that is easy to use, can be operated by hand without the need for special tools, that readily lends itself to closely-spaced capillaries, and that requires a relatively limited amount of manipulation to remove and replace capillaries.

SUMMARY OF THE INVENTION

The present invention satisfies these needs. In accordance with the present invention, a capillary assembly includes a capillary tube and first and second holders proximate first and second ends of the capillary tube. The first holder has protruding portions on opposite sides of a body. The second holder includes a body holding a portion of the capillary tube. The second holder includes windows formed in opposite sides of the body with the windows exposing a portion of the capillary tube.

The protruding portions may be cylindrical. The first holder may include a flat portion and a stop that defines an area between the protruding portions. The stop is of sufficient size to be grasped between the fingertips of a user. The first holder may further include orientation means such as a notch or other structure formed into an edge of the holder.

The present invention also contemplates a capillary retaining system. Such a system may include a capillary assembly, a first retainer for retaining a first end of the capillary assembly, and a second retainer for retaining a second end of the capillary assembly. Such a system may alternatively comprise the first and second retainers that are useful with a capillary assembly, but wherein the system does not include the capillary assembly itself. As a further alternative, such a system may also include a capillary assembly useful with first and second retainers, but wherein the system does not include the first and second retainers.

The capillary assembly may include first and second holders. The first retainer includes means for removably retaining the first holder, and the second retainer includes means for removably retaining the second holder. In one embodiment, the first retainer includes a base, an opening in the base, and clips fixed with respect to the base. The clips include engaging means for releasably engaging protruding portions of the first holder.

The second retainer may include in one embodiment a retainer body defining a central opening sized to receive the second holder. Opposite bores in the retainer body intersect the central opening and are sized to receive end barrels of an optical cable, the end barrel retaining optical fibers and defining reduced portions. Retainer clips or locks slidably carried by the second retainer include means for removably engaging the barrel reduced portions. Such means may comprise a collar, and the collar can be part of a keyhole shaped opening in the retainer clips.

The first retainer can include orientation means that orients the first holder when it is received by the first retainer. The second retainer may likewise include such orientation means for similarly orientating the second holder when it is received by the second retainer.

The present invention also contemplates a method of using a capillary assembly, including installing the first holder of the capillary assembly in the first retainer, installing the second holder in the second retainer, installing first and second optical cable end barrels in the second retainer, the barrels being received by the second holder windows of the capillary assembly, and operating the second retainer locks to capture the reduced portion of each optical cable barrel by the lock.

In accordance with another important aspect of the present invention, a capillary holding system for holding a capillary tube having a first end and a second end, comprises (a) a first capillary holding portion of the capillary tube proximate the first end, the first holder comprising protrusions for cooperation and removable engagement with the capillary retaining system; (b) a second capillary holder for holding a portion of the capillary tube proximate the second end, wherein the second holder is suitable for cooperation and removable engagement with a capillary retaining system; and (c) a capillary retaining system comprising a first retainer for removably engaging the first capillary holder, the first retainer comprising a base, an opening in the base sized to receive the first holder; and a second retainer for removably engaging the second capillary holder, the second retainer comprising a retainer body defining a first opening sized to receive the second holder.

The first retainer can further comprise a clamp disposed on the base proximate the opening, the clamp comprising an arm for releasably engaging the protrusions on the first holder to urge the first holder against the base. Preferably, the first holder protrusions comprise a flange, and the first holder further comprises a first portion proximate the first end of the capillary tube and extending from the flange. The first holder can further comprise a second portion extending from the flange away from the first end of the capillary tube, the second portion providing an area of sufficient size to be gripped between fingertips of the user. Preferably, the first portion and the flange of the first holder are electrically conductive to form an electrode for capillary electrophoresis.

The second retainer can further comprise secondary openings defined in the retainer body, and a level pivotally mounted in the secondary openings in order to pry the second holder out of the first opening when the level is rotated from a first level position to a second level position. The second holder can further comprise windows formed in its opposite sides for exposing a portion of a capillary tube held by the second holder.

The present invention also provides a capillary holding system for holding at least one capillary tube having a first end and a second end, the system comprising the first capillary holder and the second capillary holder as described above, and a capillary retaining system comprising a plurality of first and second retainers as described above. In this embodiment, the capillary system can further comprise a mounting surface, wherein the first retainers are disposed on the mounting surface substantially adjacent to one another, and wherein the second retainers are disposed on the mounting surface substantially adjacent to one another, whereby a plurality of first and second capillary holders can be disposed in the retaining systems adjacent to one another.

Preferably, the first retainer bases are joined to form a single base for the plurality of the first retainers, and the first retainer clamps are joined to form a single clamp disposed on the single base, with the single clamp having a plurality of arms for releasably engaging the protrusions on a plurality of first holders to urge the first holders against the single base.

In yet another embodiment of the invention, the second retainer further comprises retainer locks pivotally carried by the second retainer in openings defined in the retainer body, wherein the retainer locks comprise means for removably engaging end barrels of optical cables useful with the capillary retaining system. Preferably, each retainer lock comprises a spring clip having a pair of substantially parallel legs, each leg having an upper and a lower end, with the upper end of the legs joined and the legs spaced apart to receive and engage end barrels of the optical cables between the legs, wherein the horizontal lower end of the legs are pivotally disposed in openings in the retainer body.

BRIEF DESCRIPTION OF THE DRAWINGS

These and other advantages and aspects of the present invention will be apparent with reference to the Figures in which:

FIG. 16 is a view of the capillary holders of FIG. 15, holding a capillary tube;

FIG. 17 is a section view of the first holder of FIG. 16;

FIG. 18 is a partial section view of the tip of the first capillary holder shown in FIG. 17;

FIG. 19 is a side view of the second holder shown in FIG. 16;

FIG. 20 is a section view of the second holder shown in FIG. 19 taken along line 6—6 thereof;

FIG. 21 is an enlarged view of the bottom of the input recess of FIG. 20;

FIG. 22 is an enlarged section view of the detection end of FIG. 20;

FIG. 23 is an exploded view of the first retainer of FIG. 15;

FIG. 24 is a top view of the first retainer of FIGS. 15 and 23 along line 10—10 thereof;

FIG. 25 is a section view of the first retainer of the system of FIG. 24 along line 11—11;

FIG. 26 is a partial cross-section view of the first retainer of FIG. 24 taken along line 12—12 thereof;

DETAILED DESCRIPTION

Figure 1:
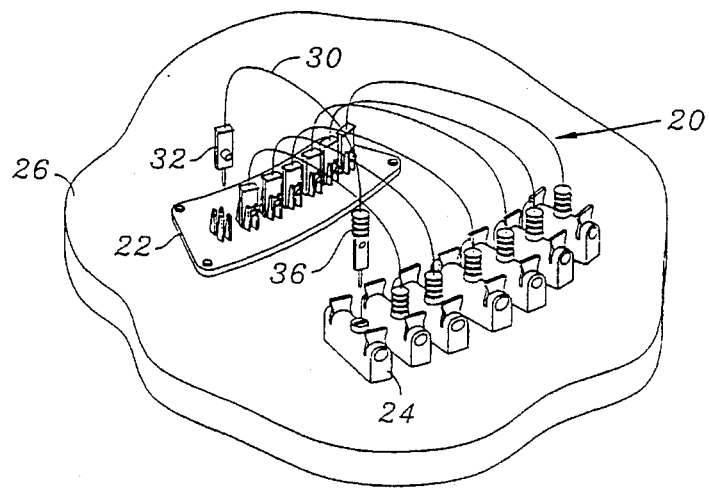
FIG. 1 is a perspective view of capillary assemblies and a capillary retaining system in accordance with the present invention.

With reference to FIG. 1, a plurality of capillary assemblies 20 may be removably retained by sample end retainers 22 and detection end retainers 24. The sample end retainers 22 and detection end retainers 24 may be, for example, fixed to a mounting platform or base 26 that is part of a capillary electrophoresis analyzer (not shown). A suitable electrophoresis analyzer is disclosed, for example, in as U.S. Pat. No. 5,356,525 issued Oct. 8, 1994 identified above, and other such suitable analyzers will be apparent to those skilled in the art.

Figure 2:
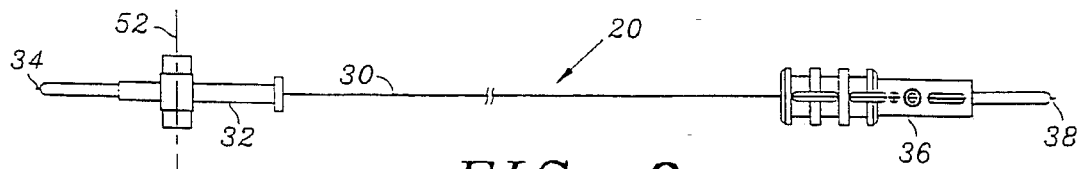
FIG. 2 is a view of a capillary assembly of FIG. 1.

With reference to FIG. 2, a capillary assembly 20 includes a capillary 30, a first or sample end holder 32 fixed proximate a sample induction end 34 of the capillary 30, and a second or detection end holder 36 fixed proximate a detection end 38 of the capillary 30. The capillary 30 is preferably conventional silica quartz glass formed with a thin conformal coating of a polyamide, having an inside diameter within a range of about five microns to two hundred microns and more particularly in a range of approximately twenty five microns to seventy five microns, and an outer diameter of about one hundred fifty microns to three hundred seventy five microns, respectively.

Figure 3:
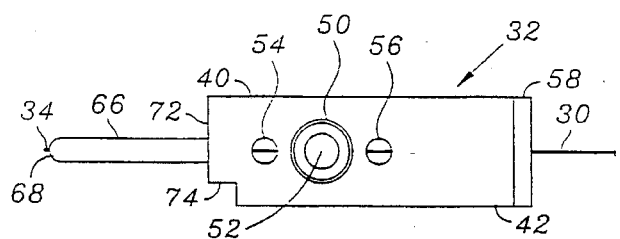
FIG. 3 is a side view of the sample end holder of the capillary assembly of FIG. 2.
Figure 4:
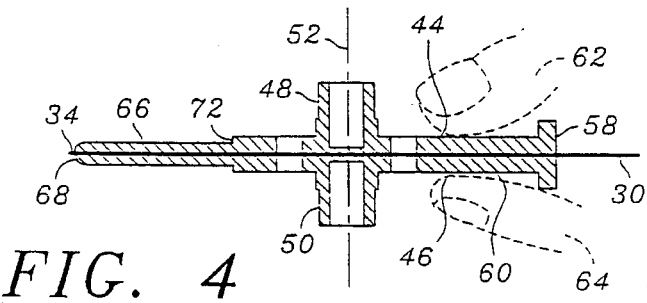
FIG. 4 is a section view of the sample end holder of the capillary assembly of FIG. 2.

The sample end holder 32 (FIGS. 2–4) has a body 40 including a generally flat portion 42 having opposite sides 44 and 46, and fastener bodies 48, 50 projecting from the opposite sides 44, 46. The fastener bodies 48, 50 are cylindrical and are coaxially aligned along axis 52. The axis 52 is perpendicular to and intersects the capillary 30. Openings 54, 56 in the flat portion 42 provide access to the capillary 30 so that the capillary 30 can be held in place during fabrication by, for example, molding of the sample end holder 32 onto the capillary 30. The openings 54, 56 also provide stress relief for the capillary 30 otherwise associated with the cooling of the sample end holder 32 material, preferably black plastic, during molding.

A stop 58 is formed at one end of the flat portion 42, the stop projecting perpendicularly with respect to the flat portion 42. An area 60 between the fastener bodies 48, 50 and the stop 58 provides a convenient gripping area between fingertips 62, 64 (shown in phantom is FIG. 4) of a user of the capillary assembly 20.

The body 40 also includes an inlet cylindrical portion 66 having a rounded end 68, the open sample induction end 34 of the capillary 30 extending slightly from the rounded end 68. An end or shoulder 72 is defined at the end of the flat portion 42 opposite from the end at which the stop 58 is formed, the end 72 having a notch 74 at one corner thereof.

Figure 6:
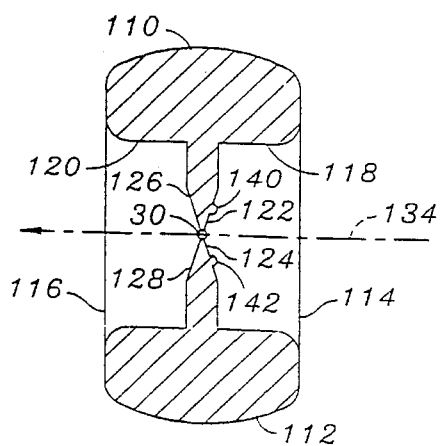
FIG. 6 is a section view of the detection end holder of FIG. 5 taken along line 6—6 thereof.
Figure 5:
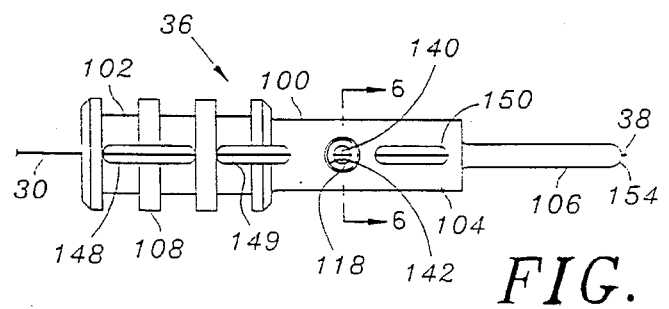
FIG. 5 is a side view of the detection end holder of the capillary assembly of FIG. 2.

The detection end holder 36 (FIGS. 5–7) has a body 100 having a handle portion 102, flat portion 104 and an outlet cylindrical portion 106. The handle portion 102 is cylindrical and includes ribs 108 that facilitate grasping between the finger tips of a user. The flat portion 104 has rounded edges 110, 112 and flat opposite surfaces 114, 116. Aligned opposing cylindrical input and output recesses 118, 120, respectively, are formed in the flat portion 104 and tapered surfaces 122, 124 and 126, 128, centered at the bottoms of the recesses 118 and 120, respectively, expose a length 130 of the capillary 30.

Figure 7:
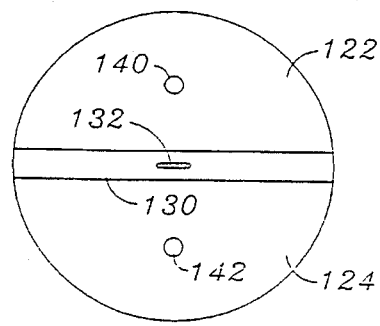
FIG. 7 is an enlarged view of the bottom of the input recess of FIG. 6.

Opposite windows are formed in the coating of the capillary 30, one of the windows 132 being illustrated in FIG. 7. The windows form an optical path 134 through the capillary 30. In the embodiment disclosed herein, the windows are about 0.001 inch by 0.008 inch. A capillary assembly utilizing windows of the type disclosed herein is described in U.S. patent application Ser. No. 07/917,640, filed Jul. 17, 1992 issued as U.S. Pat. NO. 5,312,535 on May 17, 1994, in the name of Waska et al, entitled "Capillary Electrophoresis Detection," which is incorporated herein by reference.

Targets 140, 142 are formed on the tapered surfaces 122, 124, the targets 140, 142 taking the form of small bumps or protrusions. The target 140,142 are at predetermined distances from the exposed length 130 of the capillary 30 and provide alignment references for use in removing the capillary 30 coating to form the opposing windows by, for example, burning off using a laser.

Elongated through openings 148, 149 and 150 in the detection end holder 36 are used to hold and position the capillary 30 during fabrication by, for example, molding of the detection end holder 36 onto the capillary 30. As with the openings 54, 56 in the sample end holder 32, the elongated openings 148, 149 and 150 also provide stress relief for the capillary 30 that might otherwise be associated with the cooling of the detection end holder 36 material, preferably black plastic, during molding.

The outlet cylindrical portion 106 is similar to the sample induction end cylindrical portion 66 and likewise includes a rounded end 154. The open detection end 38 extends slightly beyond the rounded end 154.

Figure 8:
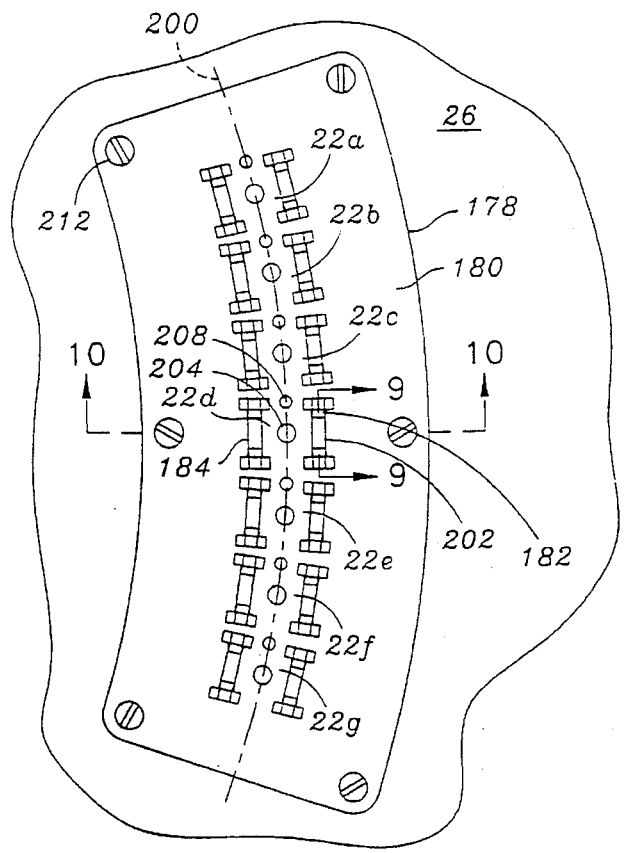
FIG. 8 is a top view of a sample end retainer of FIG. 1.
Figure 9:
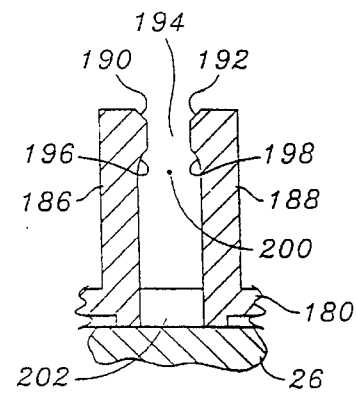
FIG. 9 is a cross-section view of the sample end retainer of FIG. 8 taken along line 9—9 thereof.

In the embodiment disclosed herein, the sample end retainers 22 are formed in a single arcuate header 178 (FIG. 8). The header 178 has a flange 180, the header 178 forming seven sample end retainers 22a–22g. The fourth sample end retainer 22d is typical of the others, and has two clips 182, 184, each of which has opposing flexible arms 186, 188, illustrated in FIG. 9 with respect to the first clip 182. The arms 186, 188 project from the flange 180 and include opposing enlarged ends 190, 192 that form a reduced entrance 194 and engagement surfaces 196, 198. The engagement surfaces 196, 198 share a common radius center point 200 and a slot 202 through the flange 180 is formed between the arms 186, 188 to increase the flexibility of the arms 186, 188.

Figure 10:
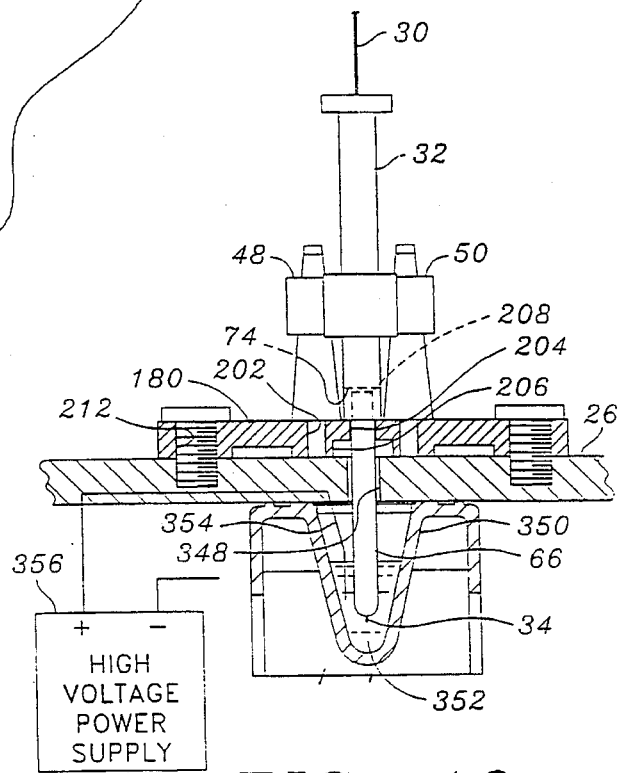
FIG. 10 is a partial cross-section view of the sample end retainer of FIG. 8 taken along line 10—10 thereof.

The two clips 182, 184 are on opposite sides of a round opening 204 (FIG. 10), the opening 204 including an enlarged portion 206 formed in the opposite side of the flange 180. A raised boss 208 between the clips 182, 184 projects from the flange 180. The boss 208 is to one side of the opening 204 and is sized to be received within the notch 74 when the sample end holder 32 is removably retained by the sample end retainer 22 as is described below. In the embodiment illustrated in FIG. 8, the sample end retainers 22a–22g are aligned in an accurate path 210.

The flange 180 may include a plurality of openings 212 that can be used for fastening the header 178 and thus the sample end retainers 22a–22g to the base 26.

Figures 11, 12:
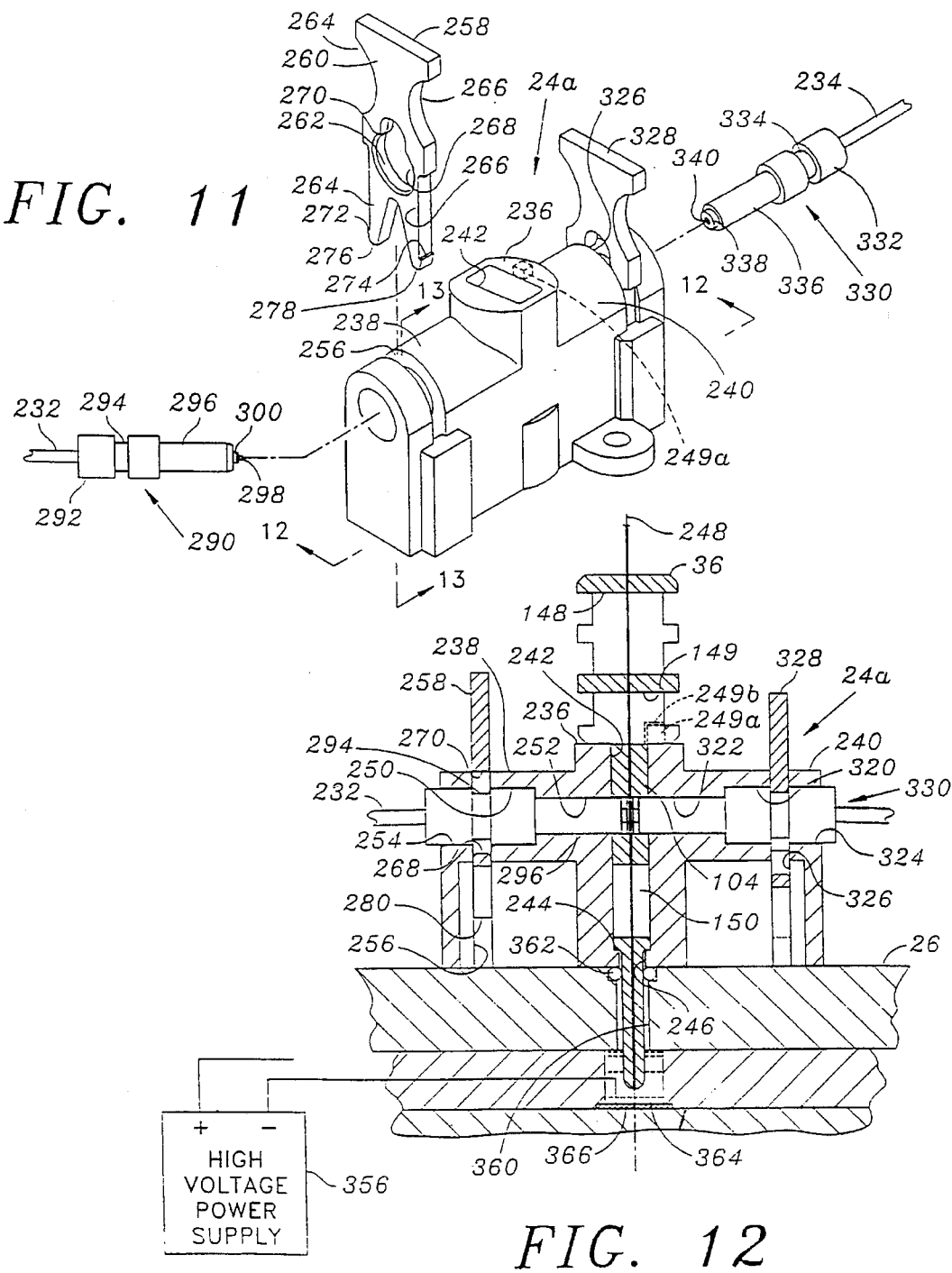
FIG. 11 is a perspective partially exploded view of a detection end retainer of the system of FIG. 1.
FIG. 12 is a partial cross-section view of the detection end retainer of FIG. 11 taken generally along line 12—12 thereof, but with a detection end holder and input and output optical cables installed and an input lock in an unlocked position and an output lock in a locked position.

The detection end retainers 24 (FIGS. 11 and 12) are adapted to retain the capillary assemblies 20 and input and output optical cables 232, 234. The detection end retainers 24 are typical and one of such retainers 24a is shown in FIG. 11. The detection end retainer 24a includes a holder portion 236 and input and output cable receivers 238,240. The holder portion 236 has a vertical elongated opening 242 sized to receive the flat portion 104 of the detection end retainer 36, the elongated opening 242 having an end 244 with a round opening 246 sized to receive the outlet cylindrical portion 106. The round opening 246 is centered with respect to the elongated opening 242 with a central axis 248 common to both such that the flat portion 104 and the outlet cylindrical portion 106 can be received within the holder portion 236 with the outlet cylindrical portion 106 extending out of the round opening 246.

Figure 13:
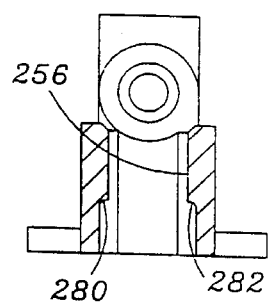
FIG. 13 is a partial cross-section view of the detection end retainer of FIG. 11 taken along line 13—13 thereof.

The input cable receiver 238 defines an input bore 250 having a reduced portion 252 and a larger portion 254, the reduced portion 252 being proximate the elongated opening 242. A vertical slot 256 intersects the larger portion 254 and is sized to receive a input lock 258. The input lock 258 has a handle portion 260, a keyhole opening 262, and legs 264,266. The handle portion 260 has indentations 266 sized to receive the fingers of a user (not shown). The keyhole opening 262 has a larger opening 268 (as illustrated in FIG. 11) and a smaller collar or key portion 270. The legs 264, 266 each include outward shoulders 272, 274 proximate ends 276, 278. The outward shoulders 272, 274 are adapted to engage inward shoulders 280, 282 (FIG. 13) in the slot 256, allowing the input lock 258 to be movably retained within the slot 256.

The input bore 250 receives an end connector 290 of the input optical cable 232. The end connector 290 has a barrel 292 with a circumferential groove 294 and a tube 296 about the end of an input optical fiber 298. A sleeve 300 projects from the end of the tube 296 and crimps the optical fiber 298 in place.

The output receiver 240 is similar to the input receiver 238, and has an output bore 320 with reduced and larger portions 322, 324 respectively, and slot 326 retaining an output lock 328. The output bore 320 is adapted to receive an end connector 330 of the output optical cable 234, the end connector 330 including a barrel 332, groove 334, tube 336 and sleeve 338 about an output fiber 340 in a similar fashion to the input end connector 290.

The detection end holder 36 may also be keyed with respect to the elongated opening 242 by the use, for example, of a boss 249a formed at the side of the elongated opening 242, which cooperates with a notch 249b formed in the handle portion 102. The boss 249a and notch 249b are shown in phantom in FIGS. 11 and 12, and function in a similar fashion to the boss 208 and notch 74 associated with the sample end retainer 22d and sample end holder 32 described above.

In use, a plurality of the capillary assemblies 20 is installed into, for example, the sample end retainer 22d and the typical detection end retainer 24. To install one of the capillary assemblies 22 onto the sample end retainer 22, the cylindrical portion 66 of the sample end holder 32 (FIG. 10) is inserted through the opening 204 in the flange 180 and an aligned opening 348 in the base 26. The sample end retainer 22 is urged toward the flange 180 and the fastener bodies 48, 50 are pressed through the reduced entrance 194, flexing the arms 186, 188 (and corresponding arms for clip 184) aside. With the shoulder 72 against the flange 178, the fastener bodies 48, 50 are engaged by the engagement surfaces 196, 198 (and similar engagement surfaces for the clip 184) as shown in phantom in FIG. 9, retaining the sample end holder 32 within the sample end retainer 22d. The boss 208 and notch 74 cooperate to index or orient the sample end holder 32 with respect to the sample end retainer 22d.

The sample induction end 34 may be, for example, disposed within a well 350 containing a dilute sample 352 to be analyzed. An electrode 354 is also in contact with the sample 352 and is connected to a high voltage power supply 356, shown in simplified block from in FIG. 10.

The detection end holder 36 of the capillary assembly 20 is installed into a respective detection end retainer 24 by inserting the flat portion 104 into the elongated opening 242 with the outlet cylindrical portion 106 passing through the round opening 246 in the holder portion 236 and through a manifold opening 360 in the base 26 that is aligned with the round opening 246. An o-ring seal 362 seals the outlet cylindrical portion 106 within a conduit in which is disposed a liquid buffer 364 in which the detection end 38 is held. An electrode 366 is connected to the other potential supplied by the high voltage power supply 356, providing an electrophoresing voltage as is well known in the art between the sample 352 and the buffer 364.

The input lock 258 is raised, the shoulders 272, 274 engaging the inward shoulders 280, 282 and aligning the center of the larger opening 268 with the centerline of the bore 250. The input optical cable 232 in inserted into the bore 250, the tube 296 being received within the input recess 118 and aligning the input fiber 298 with the optical path 134 through the window 142. The input lock 258 is operated to engage the collar or key portion 270 with the groove 294, thus retaining the input optical cable 232 within the detection end holder 36.

Similarly, the output optical cable 234 is installed into the detection end retainer 24a, the tube 336 engaging the output recess 120 and aligning the output fiber 340 with the optical path. The output lock 328 is operated to engage the groove 334. With the tubes 296 and 336 engaging the input and output recesses 118, 120, the detection end holder 36 is secured within the detection end retainer 24a.

Additional capillary assemblies 20 are similarly installed. Individual wells 350 may be provided for each of the capillary assemblies 20, and the conduit 360 may be common beneath the detection end retainers 24, providing the buffer 364 to the detection end 38 of each of the capillary assemblies 20.

Removal of the capillary assembly 20 is effected by pulling the sample end holder 32 free from the sample end retainer 22, the arms 186, 188 flexing to release the fastener bodies 48, 50. The input and output locks 258,328 are raised, the input and output cables 232, 234 are removed, and the detection end holder 36 is removed from the detection end retainer 24.

It is to be appreciated that the present invention contemplates that a single capillary assembly 20 may be retained by a single sample end retainer 22 and a single detection end retainer 24. Such may be useful, for example, if an analyzer is designed to provide a single capillary analysis at a given time. The invention also contemplates that a plurality of capillaries may be conveniently retainer as illustrated in FIG. 1, thus allowing multiple parallel capillary electrophoretic analyses to be performed simultaneously in a single analyzer.

Figure 14:
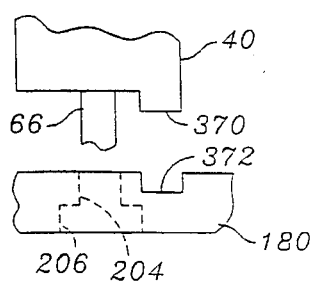
FIG. 14 is a partial side view of an alternative form of orientation means useful in the sample end holder of FIG. 3.

Moreover, the boss 208 and notch 74, as well as the boss 249a and notch 249b, are optional. For example, the boss 208 and notch 74 need not be used where orientation of the sample end holder 32 is not important with respect to a sample end retainer 22. Similarly, the boss 249a and notch 249b need not be used if the orientation of the windows through the capillary 30 are not important when the detection end holder 36 is installed in the detection end retainer 24. Additionally, other forms of orientation means can be used. For example, the notch 74 can be replaced by a protrusion 370 in the body 40 (FIG. 14) that is adapted to mate with a corresponding recess 372 in the sample end retainer flange 180. Similar structure can likewise be utilized on the detection end holder 36 and the detection end retainer 24.

Figure 15:
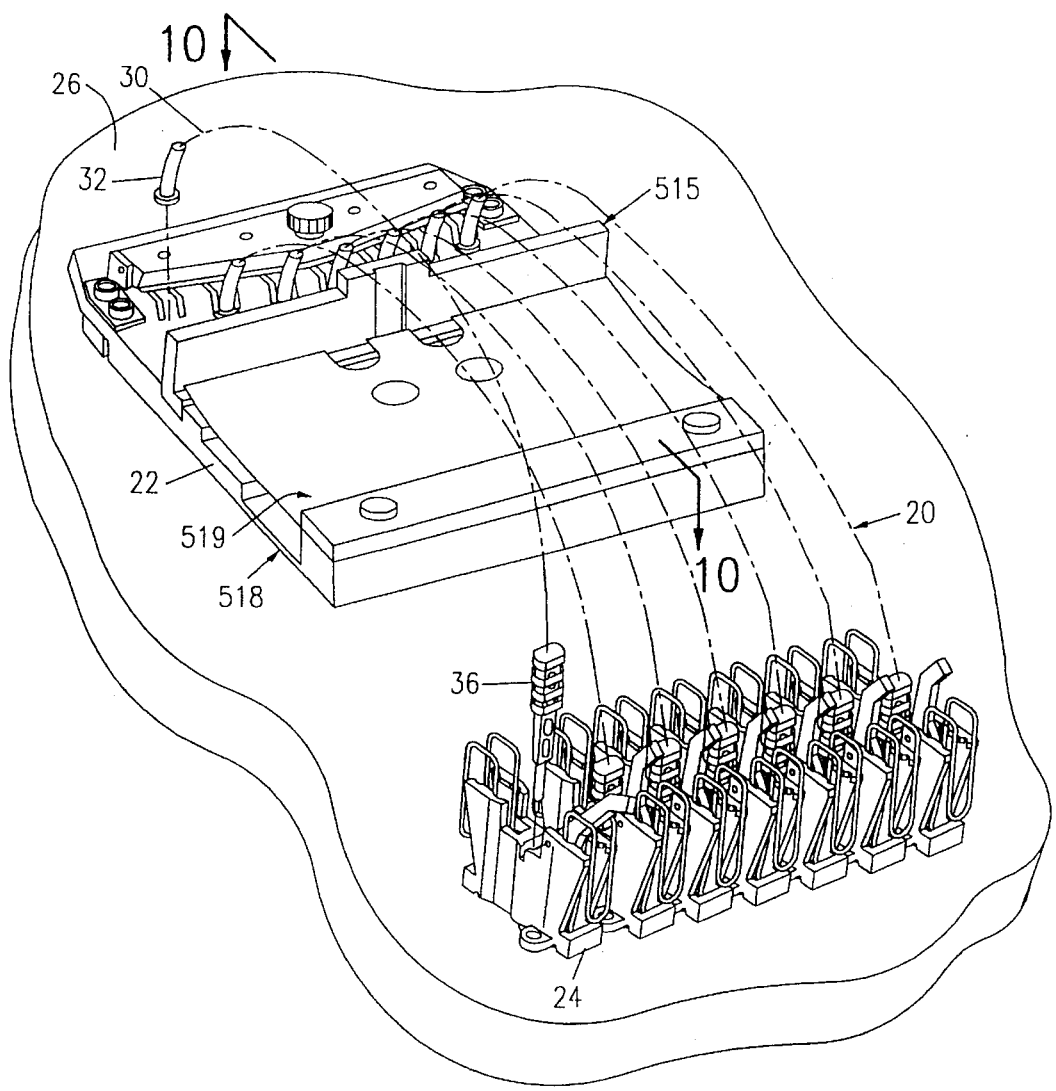
FIG. 15 is perspective view of another embodiment of capillary holders and a capillary retaining system in accordance with the present invention.

FIG. 15 shows another embodiment of the present invention. A plurality of capillary holders 32 and 36, or capillary assemblies 20 can be removably retained by sample end retainers 22 and detection end retainers 24. The sample end retainers 22 and detection end retainers 24 may be, for example, fixed to a mounting platform or base 26 that is part of a capillary electrophoresis analyzer (not shown). A suitable electrophoresis analyzer is disclosed, for example, in U.S. Pat. No. 5,356,525 issued Oct. 8, 1994 identified above, and other such suitable analyzers will be apparent to those skilled in the art.

With reference to FIG. 16, a capillary assembly 20 includes a capillary 30, a first or sample end holder or guide 32 fixed proximate a sample induction end 34 of the capillary 30, and a second or detection end holder 36 fixed proximate a detection end 38 of the capillary 30.

The sample end guide 32 (FIGS. 16–18) has a cylindrical fitting 40, including a round flange 42, which is made from an electrically conductive plastic or metal and is affixed to a length of hypodermic tubing 66, which protrudes from both sides of fitting 40. One end of the capillary 30 is inserted into the hypodermic tubing 66 and affixed to the end of the tubing 66 with epoxy 56, which must form a seal between the sample end of capillary 34 and the tubing 66. A length of flexible plastic tubing 54 is pushed over the capillary 30 and bonded to the fitting 40 and capillary 30. The plastic tubing 54 acts as a strain relief to protect the capillary tubing 30 and provides a grip point for removing or inserting the first holder 32 into the sample end retainer 22.

The detection end holder 36 (FIGS. 19–22) has a body 100 having a handle portion 102, flat portion 104 and an outlet cylindrical portion 106. The handle portion 102 is semi-cylindrical with opposing flats and includes ribs 108 that facilitate grasping between the finger tips of a user. The flat portion 104 has rounded edges 110, 112 and flat opposite surfaces 114, 116. Aligned opposing conical input and output recesses 118, 120, respectively, are formed in the flat portion 104 and tapered surfaces 122, 124 and 126, 128, centered at the bottoms of the recesses 118 and 120, respectively, expose a length 130 of the capillary 30.

Opposite windows 132 are formed in the coating of the capillary 30, one of the windows 132 being illustrated in FIG. 21. The windows form an optical path 134 through the capillary 30. In the embodiment disclosed herein, the windows 132 are about 0.001 inch by 0.008 inch.

Target 140 is formed on the tapered surface 122, the target 140 taking the form of a small conical bump. The target 140 is at a predetermined distance from the exposed length 130 of the capillary 30 and provides alignment references for use in removing the capillary 30 coating to form the opposing windows 132 by, for example, burning off using a laser.

Elongated through openings 148, 149 and 150 in the detection end holder 36 are used to hold and position the capillary 30 during fabrication by, for example, molding of the detection end holder 36 onto the capillary 30. The elongated openings 148, 149 and 150 provide stress relief for the capillary 30 that might otherwise be associated with the cooling and shrinking of the detection end holder 36 material, preferably black plastic, during molding. A key 37 is molded into one side of the body 100 to align the holder 36 in the retainer 24.

The outlet cylindrical portion 106 includes a reduced diameter portion 153 and rounded end 154. The open detection end 38 of the capillary 30 extends slightly beyond the rounded end 154.

Referring to FIGS. 23–26, the sample end guide 32 is inserted into one of seven counterbored holes 500 formed in an arcuate pattern in a plastic header 501 (FIGS. 23 and 24). A pivoting retainer assembly is comprised of an electrode clip 502, electrode block 503, key pull 504, spring 505, four attachment screws 506, and a key pull bar 512. A retainer sub-assembly comprises two brackets 508, which are attached to the header 501 by means of screws 509, washers 510, and nut plates 511. A key pull bar 512 fits through a slot 513 in the header 501, and when given a 90 degree twist locks the assembly into position. Electrode clip 502 includes fingers 527 formed in pairs, each pair of fingers 527 providing a spring load which is able to hold down the flange 42 of the sample end guide 32 in the counterbored hole 500 in the header (see FIG. 15). The retainer sub-assembly rests on two positional stops 514 affixed to the header 501. These stops 514 assure proper preload of the fingers on the sample end guide flanges 42. A divider 515 is affixed to the header 501 to position the optical cables relaying the signal to the system electronics. The divider 515 organizes the optical cables and prevents the cables from interfering with the capillaries and retention system.

A capillary seal 516 fits into a recess on the bottom side of the header 501 to prevent leakage of reagent or sample between the header 501 and manifold 517.

The header sub-assembly is attached to the manifold 517 by means of a fiberglass hinge 518 and a fiberglass clasp 519. The fiberglass clasp 519 and fiberglass hinge 518 are anchored by a hinge bar 520, hinge spacer 521, nut plate 522, screws 523 and caps 524.

FIGS. 24, 25 and 26 show a top view and two section views, respectively, of the assembly of sample end capillary header 501. FIG. 25 shows the capillary sample end guide 32 extending through the header 501 and into the sample sector 525.

This arrangement allows easy removal of the sample end guides 32 from the header 501 using a slotted screwdriver or coin. The entire header assembly may also be removed by removing two screws 526. This allows access to the space between the header assembly and the manifold 517 for cleaning.

Figure 27:
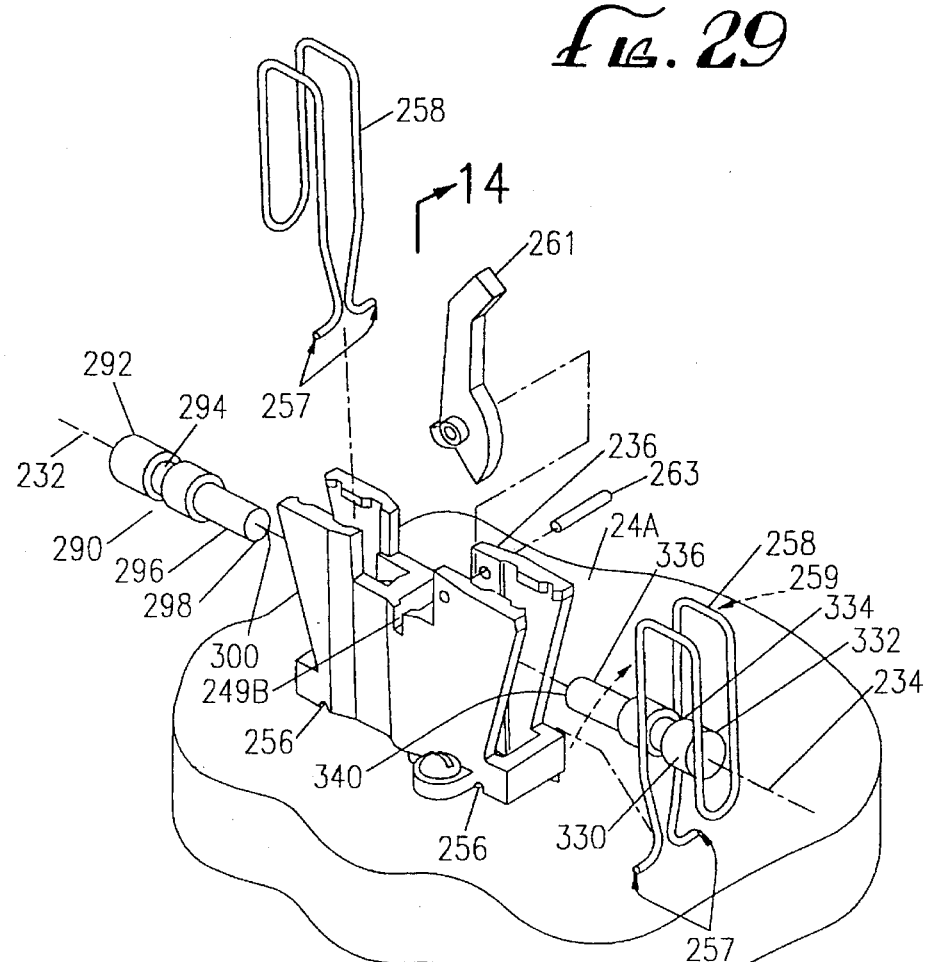
FIG. 27 is an exploded view of the second retainer of FIG. 15.
Figure 28:
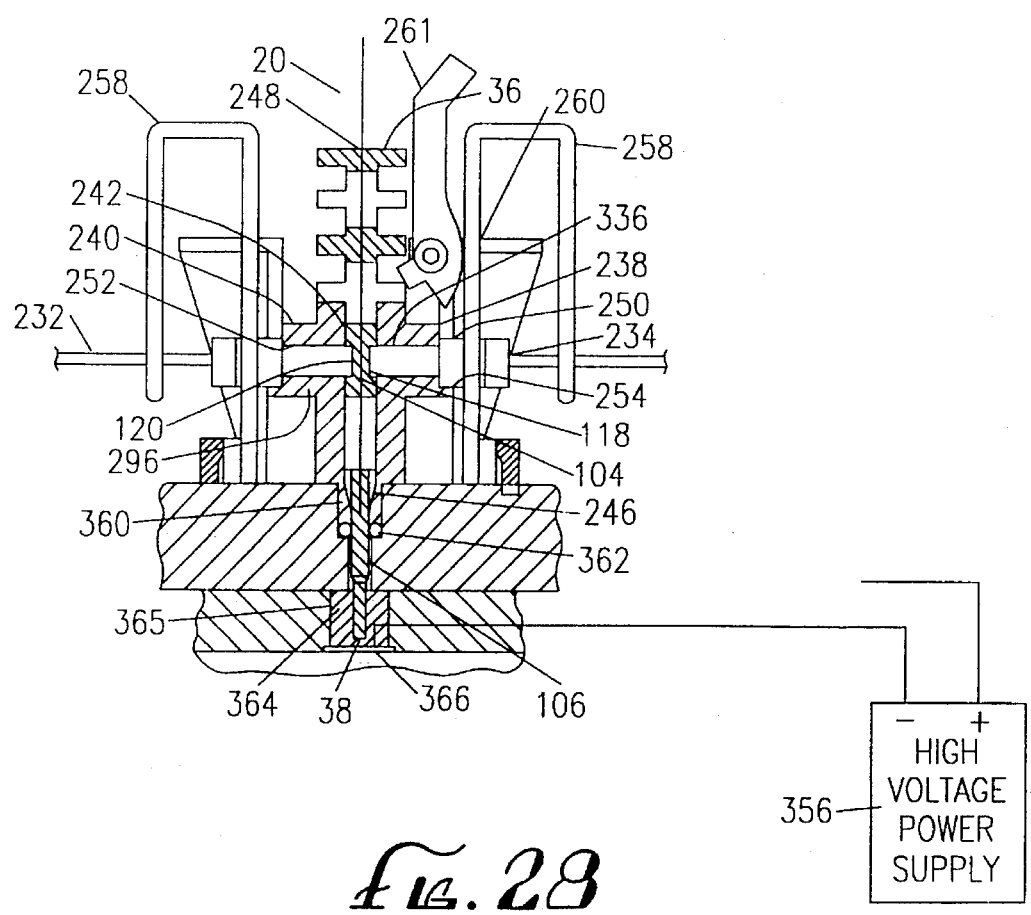
FIG. 28 is a section view of the second retainer of FIG. 27 taken along line 14—14 thereof, showing the installed position of the second holder and fiber optic cables.

The detection end retainers 24 (FIGS. 15, 27, 28 and 29) are adapted to retain the detection end retainers 24 or the capillary assemblies 20 and input and output optical cables 232, 234. The detection end retainers 24 are typical and one of such retainers 24a is shown in FIG. 27. The detection end retainer 24a includes a holder portion 236 and input and output cable receivers 238,240. The holder portion 236 has a vertical elongated opening 242 sized to receive the flat portion 104 of the detection end retainer 36, the elongated opening 242 having an end 244 with a round opening 246 sized to receive the outlet cylindrical portion 106. The round opening 246 is centered with respect to the elongated opening 242 with a central axis 248 common to both such that the flat portion 104 and the outlet cylindrical portion 106 can be received within the holder portion 236 with the outlet cylindrical portion 106 extending out of the round opening 246.

The input cable receiver 238 (FIG. 28) defines an input bore 250 having a reduced portion 252 and a larger portion 254, the reduced portion 252 being proximate the elongated opening 242. Two horizontal slots 256 intersect the holder portion 236 and are sized to receive the horizontal legs 257 of a wire spring clip 258. The slots 256 serve as hinging points for pivoting the clips 258, The spring clips 258 function as latches to force the fiberoptic end connectors 290, 330 against the flat bottom surfaces of the opposing cylindrical input and output recesses 118, 120 (FIG. 20). The wire spring clips 258 are installed in the holder 236 by squeezing the opposing sides 259 of the spring clips 258 until the vertical portion of the wire clips engage circumferential grooves 294 and 334 formed in the input and output fiberoptic connectors 290, 330. Tube ends 296 and 336 of the fiberoptic connectors engage input and output bores 250 and 320 respectively. By continuing to rotate the wire springs 258 toward the capillary window, the wire spring 258 engages a notch 265 formed in the holder 236. In this position the wire spring 258 exerts a steady spring load between the connector and the recesses 118, 120, which eliminates any gaps where light ban escape and exerts a preload such that flexing of the fiberoptic cables 232, 234 or movement caused by temperature cycling are compensated for by the spring action of 258, thus reducing the variability of the U.V. light beam.

A lever 261 is mounted in the holder 236 by means of a pin 263. The lever is provided to pry the capillary detection end 36 out of the slot in the holder 236, when the wire springs 258 are moved to the second position (FIG. 29), wherein the wire legs are engaged in the outboard slots 262 in the body of the holder 236. In this position the fiberoptic tubes 296,336 are safely disengaged from the capillary detection end 36. This level provides smooth release from the holder to avert damage to capillary.

The detection end holder 36 may also be keyed with respect to the elongated opening 242 by the use, for example, of a notch 249B formed at the side of the elongated opening 242, which cooperates with a boss 37 (FIG. 19) formed in the handle portion 102. The boss 37 and notch 249B are shown in FIGS. 19 and 27, respectively.

In use, a plurality of the capillary assemblies 20 is installed into, for example, the sample end retainer 24 (FIG. 15). To install one of the capillary assemblies 20 into the sample end retainer 22 the retainer sub-assembly with the electrode clip 502 is rotated out of the way by twisting the key pull fastener 504 one quarter turn. The cylindrical portion 60 of the sample end holder 32 (FIG. 3) is inserted through the opening 500 in the header 501 and an aligned opening 348 in the base 517. The sample end guide 32 is urged toward the counterbore 500 in the header 501. With the shoulder of the flange 42 against the bottom of the counterbore, the electrode clip 502 is rotated into position so that two fingers rest on top of each flange 42 and the key pull fastener 504 is tightened.

The sample induction end 34 may be, for example, disposed within a well 525 containing a dilute sample 352 to be analyzed. An electrode 354 is also in contact with the sample 352 and is connected to a high voltage power supply 356, shown in simplified block form in FIG. 25.

Figure 29:
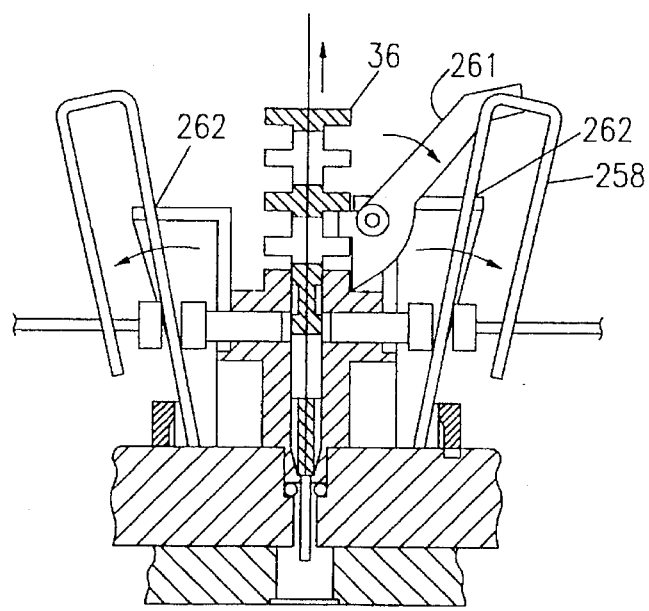
FIG. 29 is a section view of the second retainer of FIG. 27 showing the retracted position of both the second holder and the fiber optic cables.

The wire spring clips 258 are rotated out to the first notch 262, which retracts the fiberoptic connectors 290, 330 from the capillary recesses (FIG. 29). The lever 261 is rotated toward the center of the holder 236.

The detection end holder 36 of the capillary assembly 20 (FIGS. 16, is installed into a respective detection end retainer 24 by inserting the flat portion 104 into the elongated opening 242 with the outlet cylindrical portion 106 passing through the round opening 246 in the holder portion 236 and through a manifold opening 360 in the base 26 that is aligned with the round opening 246. An o-ring seal 362 seals the outlet cylindrical portion 106 within a conduit in which is disposed a liquid buffer 364 in which the detection end 38 is held. An electrode is connected to the other potential supplied by the high voltage power supply 356, providing an electrophoresing voltage as is well known in the art between the sample 352 and the buffer 364.

The wire spring clips 258, which are straddling the fiberoptic connectors (input 234; output 232)in the grooves 294, 334, are rotated toward the center of the holder 236 until the legs engage the second notches 260 in the holder 236.

Additional capillary assemblies 20 are similarly installed. Individual wells 350 may be provided for each of the capillary assemblies 20, and the conduit may be common beneath the detection end retainers 24, providing the buffer to the detection end 38 of each of the capillary assemblies 20.

The capillary assemblies 20 are removed from the sample end retainer 24 (FIG. 15) as follows. To remove one of the capillary assemblies 20 from the sample end retainer 22 the retainer sub-assembly with the electrode clip 502 is rotated out of the way by twisting the key pull fastener 504 one quarter turn. The cylindrical portion 40 of the sample end holder 32 (FIG. 17) is removed through the opening 500 in the header 501. The sample end guide 32 is pulled away from the counterbore 500 in the header 501.

At the detector end, the wire spring clips 258 which are straddling the fiberoptic connectors (input 234, output 232) in the grooves 294, 334, are rotated out to the first notch 262, which retracts the fiberoptic connectors 290, 330 from the capillary recesses (FIG. 29). The lever 261 is rotated toward the outside of the holder 236. This motion pries the capillary detector 36 from the hole 242 in the holder 236.

It is to be appreciated that the present invention contemplates that a single capillary assembly 20 may be retained by a single sample end retainer 22 and a single detection end retainer 24. Such may be useful, for example, if an analyzer is designed to provide a single capillary analysis at a given time. The invention also contemplates that a plurality of capillaries may be conveniently retained as illustrated in FIG. 15, thus allowing multiple parallel capillary electrophoretic analyses to be performed simultaneously in a single analyzer.

Moreover, the boss 37 and notch 249B are optional. The boss 37 and notch 249B need not be used if the orientation of the windows through the capillary 30 are not important when the detection end holder 36 is installed in the detection end retainer 24. Additionally, other forms of orientation means can be used.

The present invention is not to be limited to the particular embodiments disclosed herein but is instead to be accorded the fully scope of the appended claims and all equivalents thereto.

What is claimed is:

1. A capillary holding system for holding a capillary tube having a first end and a second end, the system comprising:
   (a) a first capillary holder for holding a portion of the capillary tube proximate the first end, the first holder comprising protrusions for cooperation and removable engagement with a capillary retaining system;
   (b) a second capillary holder for holding a portion of the capillary tube proximate the second end, wherein the second holder is suitable for cooperation and removable engagement with a capillary retaining system; and
   (c) a capillary retaining system comprising:
      (i) a first retainer for removably engaging the first capillary holder, the first retainer comprising a base, an opening in the base sized to receive the first holder, and means for mechanically interlocking with the protrusions of the first capillary holder to urge the first capillary holder against the base; and
      (ii) a second retainer for removably engaging the second capillary holder, the second retainer comprising a retainer body defining a first opening sized to receive the second holder.

2. The capillary holding system of claim 1 wherein the interlocking means of the first retainer comprises a clamp disposed on the base proximate the opening, the clamp comprising an arm for releasably engaging the protrusions on the fist holder to urge the first holder against the base.

3. The capillary holding system of claim 1 wherein the second retainer further comprises secondary openings defined in the retainer body, and a lever pivotally mounted in the secondary openings in order to pry the second holder out of the first opening when the lever is rotated from a first lever position to a second lever position.

4. The capillary holding system of claim 1 wherein the second holder has opposing sides and further comprises windows formed in the opposing sides, the windows exposing a portion of the capillary tube.

5. The capillary holding system of claim 1 wherein the first holder protrusions comprise a flange.

6. The capillary holding system of claim 5 wherein the first holder further comprises a first portion proximate the first end of the capillary tube and extending from the flange.

7. The capillary holding system of claim 6 wherein the first holder further comprises a second portion extending from the flange away from the first end of the capillary tube, the second portion providing an area of sufficient size to be gripped between fingertips of a user.

8. The capillary holding system of claim 7 wherein the first and the second portions of the first holder are cylindrical.

9. The capillary holding system of claim 7 wherein the first portion of the first holder is tapered away from the flange to facilitate insertion of the first holder in the opening of the first retainer, and wherein the second portion of the first holder is cylindrical.

10. The capillary holding system of claim 9 wherein the system further comprises a hypodermic tube concentric with the capillary tube and disposed between the first holder and the capillary tube.

11. The capillary holding system of claim 7 wherein the first portion and the flange are electrically conductive to form an electrode for capillary electrophoresis.

12. The capillary holding system of claim 7 wherein the first capillary holder is electrically conductive to form an electrode for capillary electrophoresis.

13. The capillary holding system of claim 7 wherein the second portion is electrically conductive to form an electrode for capillary electrophoresis.

14. The capillary holding system of claim 13 wherein the first holder further comprises a nonconductive sleeve covering the second portion.

15. The capillary holding system of claim 1 wherein the second holder further comprises an outlet portion proximate the second end of the capillary tube, and a flat portion proximate the outlet portion, the flat portion comprising orientation means so that the second holder can engage the second retainer only in a predetermined direction.

16. The capillary holding system of claim 15 wherein the second holder flat portion further comprises an edge adjacent the outlet portion.

17. The capillary holding system of claim 16 wherein the second holder orientation means comprises a notch formed into the second holder flat portion.

18. The capillary holding system of claim 16 wherein the second holder orientation means comprises a protrusion formed into the second holder flat portion.

19. A capillary holding system for holding a capillary tube having a first end and a second end, the system comprising:
   (a) a first capillary holder for holding a portion of the capillary tube proximate the first end, the first holder comprising protrusions for cooperation and removable engagement with a capillary retaining system;
   (b) a second capillary holder for holding a portion of the capillary tube proximate the second end, the second holder having opposing sides and comprising windows formed in the opposing sides, the windows exposing a portion of the capillary tube, wherein the second holder is suitable for cooperation and removable engagement with a capillary retaining system;
   (c) a capillary retaining system comprising:
      (i) a first retainer for removably engaging the first capillary holder, the first retainer comprising a base, an opening in the base sized to receive the first holder, and a clamp disposed on the base proximate the opening, the clamp comprising an arm for releasably engaging the protrusions on the first holder to urge the first holder against the base; and
      (ii) a second retainer for removably engaging the second capillary holder, the second retainer comprising a retainer body defining a first opening sized to receive the second holder, the second retainer further comprising secondary openings defined in the retainer body, and a lever pivotally mounted in the secondary openings in order to pry the second holder out of the first opening when the lever is rotated from a first lever position to a second lever position.

20. The capillary holding system of claim 19 wherein the first holder protrusions comprise a flange, and wherein the first holder further comprises a first portion proximate the first end of the capillary tube and extending from the flange, and a second portion extending from the flange away from the first end of the capillary tube, the second portion providing an area of sufficient size to be gripped between fingertips of a user.

21. The capillary holding system of claim 20 wherein the system further comprises a hypodermic tube concentric with the capillary tube and disposed between the first holder and the capillary tube, and wherein the first portion and the flange are electrically conductive to form an electrode for capillary electrophoresis.

22. The capillary holding system of claim 20 wherein the second holder further comprises an outlet portion proximate the second end of the capillary tube, and a flat portion proximate the outlet portion, the flat portion comprising orientation means so that the second holder can engage the second retainer only in a predetermined direction.

23. A capillary holding system for holding at least one capillary tube having a first end and a second end, the system comprising:
  (a) a first capillary holder for holding a portion of the capillary tube proximate the first end, the first holder comprising protrusions for cooperation and removable engagement with a capillary retaining system;
  (b) a second capillary holder for holding a portion of the capillary tube proximate the second end, the second holder having opposing sides and comprising windows formed in the opposing side, the windows exposing a portion of the capillary tube, wherein the second holder is suitable for cooperation and removable engagement with a capillary retaining system; and
  (c) a capillary retaining system comprising:
    (i) a plurality of first retainers, each first retainer being capable of removably engaging the first capillary holder, and comprising a base, an opening in the base sized to receive the first holder, and means for mechanically interlocking with the protrusions of the first capillary holder to urge the first capillary holder against the base; and
    (ii) a plurality of second retainers, each second retainer being capable of removably engaging the second capillary holder, and comprising a retainer body defining a first opening sized to receive the second holder.

24. The capillary holding system of claim 23 further comprising a mounting surface, wherein the first retainers are disposed on the mounting surface substantially adjacent to one another, and wherein the second retainers are disposed on the mounting surface substantially adjacent to one another, whereby a plurality of first and second capillary holders can be disposed in the first and second retainers adjacent to one another.

25. The capillary holding system of claim 24 wherein the interlocking means of each first retainer comprises a clamp disposed on the retainer base proximate the opening, the clamp comprising an arm for releasably engaging the protrusions on the first holder to urge the first holder against the base.

26. The capillary retaining system of claim 25 wherein the first retainer bases are joined to form a single base for the plurality of the first retainers, and wherein the first retainer clamps are joined to from a single clamp disposed on the single base, with the single clamp having a plurality of arms for releasably engaging the protrusions on a plurality of first holders to urge the first holders against the single base.

27. The capillary holding system of claim 24 wherein each second retainer further comprises secondary openings defined in the retainer body, and a lever pivotally mounted in the secondary openings in order to pry the second holder out of the first opening when the lever is rotated from a first lever position to a second lever position.

28. A capillary retaining system suitable for receiving optical cables having end barrels retaining optical fibers, the retaining system comprising:
  (a) a capillary holder system for holding a capillary tube having a first end and a second end, comprising:
    (i) a first capillary holder for holding a portion of the capillary tube proximate the first end, the first holder comprising protrusions for cooperation and removable engagement with a capillary retaining system; and
    (ii) a second capillary holder for holding a portion of the capillary tube proximate the second end, the second holder comprising a flattened portion having opposing sides, the flattened portion comprising opposite aligned recesses formed in the opposing sides of the flattened portion, the recesses being sized to receive the end barrels of the optical cables, wherein the recesses expose the capillary tube, and wherein the second holder is suitable for cooperation and removable engagement with a capillary retaining system;
  (b) a first retainer for releasably engaging the first capillary holder, the first retainer comprising a base, an opening in the base sized to receive the first holder, and a clamp disposed on the base proximate the opening, the clamp comprising an arm for releasably engaging the protrusions on the first holder to urge the first holder against the base; and
  (c) a second retainer for releasably engaging the second capillary holder, the second retainer comprising:
    (i) a retainer body defining (1) a first opening sized to receive the second holder flattened portion, and (2) opposite bores in the retainer body and intersecting the first opening, the bores sized to receive end barrels of the optical cables;
    (ii) a lever pivotally carried by the second retainer in secondary openings defined in the retainer body to pry the second holder out of the first opening when the lever is rotated from a first lever position to a second lever position; and
    (iii) retainer locks pivotally carried by the second retainer in tertiary openings defined in the retainer body, wherein the retainer locks comprise means for removably engaging end barrels of the optical cables.

29. The capillary retaining system of claim 28 wherein the first capillary holder protrusions comprise a flange, and the first holder further comprises a first cylindrical portion proximate the first end of the capillary tube and extending from the flange, and wherein the opening in the base of the first retainer is sized to receive the first cylindrical portion.

30. The capillary retaining system of claim 29 wherein the first capillary holder further comprises a second cylindrical portion extending from the flange away from the first end of the capillary tube, the second cylindrical portion providing an area of sufficient size to be gripped between fingertips of a user.

31. The capillary retaining system of claim 30 wherein the first holder is electrically conductive in order to provide an electrode for capillary electrophoresis.

32. The capillary retaining system of claim 31 wherein the first holder comprises a nonconductive sleeve covering the second portion.

33. The capillary retaining system of claim 30 wherein the first portion and the flange are electrically conductive in order to provide an electrode for capillary electrophoresis.

34. The capillary retaining system of claim 33, wherein the clamp arm further provides an electrical contact for the first portion and the flange for high voltage electrophoresis.

35. The capillary retaining system of claim 28 wherein the system further comprises a hypodermic tube concentric with the capillary tube and disposed between the first holder and the capillary tube.

36. The capillary retaining system of claim 28 wherein the system includes a plurality of first capillary holders and first retainers, and a plurality of second capillary holders and second retainers.

37. The capillary retaining system of claim 36 further comprising a mounting surface, wherein the first retainers are disposed on the mounting surface substantially adjacent to one another, and wherein the second retainers are disposed on the mounting surface substantially adjacent to one another, whereby the plurality of the first and the second capillary holders can be disposed in the first and second retainers adjacent to one another.

38. The capillary retaining system of claim 37 wherein the first retainer bases are joined to form a single base for the plurality of the first retainers, and wherein the first retainer clamps are joined to from a single clamp disposed on the single base, with the single clamp having a plurality of arms for releasably engaging the protrusions on the plurality of the first holders to urge the first holders against the single base, respectively.

39. A capillary retaining system suitable for receiving optical cables having end barrels retaining optical fibers, the retaining system comprising:
   (a) a capillary holder system for holding a capillary tube having a first end and a second end, comprising:
      (i) a first capillary holder for holding a portion of the capillary tube proximate the first end, the first holder comprising protrusions for cooperation and removable engagement with a capillary retaining system; and
      (ii) a second capillary holder for holding a portion of the capillary tube proximate the second end, the second holder comprising a flattened portion having opposing sides, the flattened portion comprising opposite aligned recesses formed in the opposing side of the flattened portion, the recesses being sized to receive the end barrels of the optical cables, wherein the recesses expose the capillary tube, and wherein the second holder is suitable for cooperation and removable engagement with a capillary retaining system;
   (b) a first retainer for releasably engaging the first capillary holder, the first retainer comprising a base, an opening in the based sized to receive the first holder, and a clamp disposed on the base proximate the opening, the clamp comprising an arm for releasably engaging the protrusions on the first holder to urge the first holder against the base; and
   (c) a second retainer for releasably engaging the second capillary holder.

40. A capillary retaining system suitable for receiving optical cables having end barrels retaining optical fibers, the retaining system comprising:
   (a) a capillary holding system for holding a capillary tube having a first end and a second, comprising:
      (i) a first capillary holder for holding a portion of the capillary tube proximate the first end, the first holder comprising protrusions for cooperation and removable engagement with a capillary retaining system; and
      (ii) a second capillary holder for holding a portion of the capillary tube proximate the second end, the second holder comprising a flattened portion having opposing sides, the flattened portion comprising opposite aligned recesses formed in the opposing sides of the flattened portion, the recesses being sized to receive the end barrels of the optical cables, wherein the recesses expose the capillary tube, and wherein the second holder is suitable for cooperation and removable engagement with a capillary retaining system;
   (b) a first retainer for releasably engaging the first capillary holder; and
   (c) a second retainer for releasably engaging the second capillary holder, the second retainer comprising:
      (i) a retainer body defining (1) a first opening sized to receive the second holder flattened portion, and (2) opposite bores in the retainer body and intersecting the first opening, the bores sized to receive end barrels of the optical cables;
      (ii) a lever pivotally carried by the second retainer in secondary openings defined in the retainer body to pry the second holder out of the first opening when the lever is rotated from a first lever position to a second lever position; and
      (iii) retainer lock pivotally carried by the second retainer in tertiary openings defined in the retainer body, wherein the retainer locks comprise means for removably engaging the end barrels of the optical cables.

41. The capillary retaining system of claim 40 wherein the engaging means of each of he retainer locks comprises a clip.

42. The capillary retaining system of claim 41 wherein each clip comprises a spring clip having a pair of substantially parallel legs, each leg having an upper and a lower end, with the upper end of the legs joined and the legs spaced apart to receive and engage end barrels of the optical cables between the legs, and wherein the horizontal lower end of the legs are pivotally disposed in the tertiary openings.

43. The capillary retaining system of claim 40 wherein the lever comprises a handle end and a lifting end, and wherein the second capillary holder includes notch in the flattened portion to receive the lifting end of the lever when prying the second holder out of the first opening of the second retainer.

44. A capillary retaining system suitable for receiving optical cables having end barrels retaining optical fibers, the retaining system comprising:
   (a) a capillary holder system for holding a capillary tube having a first end and a second end, the system comprising:
      (i) a first capillary holder for holding a portion of the capillary tube proximate the first end, the first holder being electrically conductive and comprising: (1) a flange for cooperation and removable engagement with a capillary retaining system, (2) a first cylindrical portion proximate the first end of the capillary tube and extending from the flange, (3) a second cylindrical portion extending from the flange away from the first end of the capillary tube, the second cylindrical portion providing an area of sufficient size to be griped between fingertips of a user, and (4) a nonconductive sleeve covering the second portion; and
      (ii) a second capillary holder for holding a portion of the capillary tube proximate the second end, the second holder comprising: (1) an outlet portion proximate the second end of the capillary tube, and (2) a flattened portion proximate the outlet portion, the flattened portion having opposing sides, the flattened portion comprising opposite aligned recesses formed in the opposing sides of the flattened portion, the recesses being sized to receive the end barrels of the optical cables, wherein the recesses expose the capillary tube, the flattened portion further comprising orientation means so that the second holder can cooperate with an removably engage a retaining system only in a predetermined direction;

(b) a first retainer for releasably engaging the first capillary holder, the first retainer comprising a base, an opening in the based size to receive the first cylindrical portion of the first holder, and a clamp disposed on the base proximate the opening, the clamp comprising an arm for releasably engaging the flange on the first holder to urge the first holder against the base; and (c) a second retainer for releasably engaging the second capillary holder, the second retainer comprising:

(i) a retainer body defining (1) a first opening sized to receive the second holder flattened portion, and (2) opposite bores in the retainer body and intersecting the first opening, the bores sized to receive end barrels of the optical cables;

(ii) a lever pivotally carried by the second retainer in secondary openings defined in the retainer body to pry the second holder out of the first opening when the lever is rotated from a first lever position to a second lever position; and (iii) retainer locks pivotally carried by the second retainer in tertiary openings defined in the retainer body, wherein the retainer locks comprise clips for removably engaging end barrels of the optical cables, each clip comprising a spring clip having a pair of substantially parallel legs, each leg having an upper and a lower end, with the upper end of the legs joined and the legs spaced apart to receive and engage end barrels of the optical cables between the legs, and wherein the horizontal lower end of the legs are pivotally disposed in the tertiary openings.

45. The capillary retaining system of claim 44 wherein the system further comprises a hypodermic tube concentric with the capillary tube and disposed between the first holder and the capillary tube.

46. The capillary retaining system of claim 44 wherein the system includes a plurality of first capillary holders and first retainers, and a plurality of second capillary holders and second retainers.

47. The capillary retaining system of claim 46 further comprising a mounting surface, wherein the first retainers are disposed on the mounting surface substantially adjacent to one another, and wherein the second retainers are disposed on the mounting surface substantially adjacent to one another, whereby the plurality of the first and the second capillary holders can be disposed in the first and second retainers adjacent to one anther.

48. The capillary retaining system of claim 47 wherein the first retainer bases are joined to form a single base for the plurality of the first retainers, and wherein the first retainer clamps are joined to from a single clamp disposed on the single base, with the single clamp having a plurality of arms for releasably engaging the flanges on the plurality of the first holders to urge the first holders against the single base, respectively.

49. A capillary retaining system useful for retaining a capillary assembly, the retaining system comprising:

(a) a mounting surface;

(b) a first retainer fixed to the mounting surface, the first retainer comprising a base, an opening in the base, and a clamp disposed on the base proximate the opening, the clamp comprising an arm for releasably engaging and urging a first holder of a capillary tube against the base, the capillary tube having a first end and a second end, and the first holder holding a portion of the capillary tube proximate the first end, wherein the opening is sized to receive a portion of the first capillary holder; and (c) a second retainer fixed to the mounting surface for releasably engaging a second holder of a capillary tube, the capillary tube having a first end and a second end, and the second holder holding a portion of the capillary tube proximate the second end.

50. A capillary retaining system useful for retaining a capillary assembly, the retaining system comprising:

(a) a mounting surface;

(b) a first retainer fixed to the mounting surface for releasably engaging a first holder of a capillary tube, the capillary tube having a first end and a second end, and the first holder holding a portion of the capillary tube proximate the first end; and (c) a second retainer fixed to the mounting surface, and having a retainer body defining a first opening sized to receive a second holder of a capillary tube, the capillary tube having a first end and a second end, and the second holder holding a portion of the capillary tube proximate the second end, the second retainer further comprises a lever pivotally carried by the second retainer in secondary openings defined in the retainer body to pry the second holder out of the first opening when the lever is rotated from a first lever position to a second lever position.

51. The capillary retaining system of claim 50 wherein the second retainer further comprises retainer locks pivotally carried by the second retainer in tertiary openings defined in the retainer body, wherein the retainer locks comprise clips for removably engaging end barrels of optical cables useful with the system, each clip comprising a spring clip having a pair of substantially parallel legs, each leg having an upper and a lower end, with the upper end of the legs joined and the legs spaced apart to receive and engage end barrels of the optical cables between the legs, and wherein the horizontal lower end of the legs are pivotally disposed in the tertiary openings.

52. A capillary retaining system useful for retaining a capillary assembly, the retaining system comprising:

(a) a mounting surface;

(b) a first retainer fixed to the mounting surface, the first retainer comprising a base, an opening in the base, and a clamp disposed on the base proximate the opening, the clamp comprising an arm for releasably engaging and urging a first holder of a capillary tube against the base, the capillary tube having a first end and a second end, and the first holder holding a portion of the capillary tube proximate the first end, wherein the opening is sized to receive a portion of the first capillary holder; and (c) a second retainer fixed to the mounting surface, and having a retainer body defining a first opening sized to receive a second holder of a capillary tube, the capillary tube having a first end and a second end, and the second holder holding a portion of the capillary tube proximate the second end, the second retainer further comprising a lever pivotally carried by the second retainer in secondary openings defined in the retainer body to pry the second holder out of the first opening when the lever is rotated from a first lever position to a second lever position.

53. The capillary retaining system of claim 52 wherein the second retainer further comprises retainer locks pivotally carried by the second retainer in tertiary openings defined in the retainer body, wherein the retainer locks comprise clips for removably engaging end barrels of optical cables useful with the system, each clip comprising a spring clip having a pair of substantially parallel legs, each leg having an upper and a lower end, with the upper end of the legs joined and the legs spaced apart to receive and engage end barrels of the optical cables between the legs, and wherein the horizontal lower end of the legs are pivotally disposed in the tertiary openings.

* * * * *